(12) United States Patent
Espino et al.

(10) Patent No.: US 7,265,117 B2
(45) Date of Patent: Sep. 4, 2007

(54) TOPICAL BRIMONIDINE TARTRATE FORMULATIONS THAT LACK CHLORINE DIOXIDE

(75) Inventors: Ramon L. Espino, Cleburne, TX (US); Haresh G. Bhagat, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 106 days.

(21) Appl. No.: 11/122,651

(22) Filed: May 5, 2005

(65) Prior Publication Data

US 2005/0250778 A1    Nov. 10, 2005

Related U.S. Application Data

(60) Provisional application No. 60/568,642, filed on May 6, 2004.

(51) Int. Cl.
*A61K 31/50* (2006.01)
(52) U.S. Cl. ...................... 514/249; 514/912
(58) Field of Classification Search .................... None
See application file for complete search history.

(56) References Cited

U.S. PATENT DOCUMENTS

| | | | |
|---|---|---|---|
| 3,931,319 A | 1/1976 | Green et al. | 260/567.6 |
| 4,026,945 A | 5/1977 | Green et al. | 260/567.6 |
| 4,027,020 A | 5/1977 | Green et al. | 424/248.56 |
| 4,407,791 A | 10/1983 | Stark | 424/80 |
| 4,499,077 A | 2/1985 | Stockel et al. | 424/149 |
| 4,525,346 A | 6/1985 | Stark | 424/80 |
| 4,654,208 A | 3/1987 | Stockel et al. | 424/78 |
| 4,836,986 A | 6/1989 | Ogunbiyi et al. | 422/28 |
| 5,091,528 A | 2/1992 | Gluchowski | 544/105 |
| 5,215,991 A | 6/1993 | Burke | 514/255 |
| 5,342,620 A | 8/1994 | Chowhan | 424/422 |
| 5,424,078 A | 6/1995 | Dziabo et al. | 424/661 |
| 5,603,929 A | 2/1997 | Desai et al. | 424/78.04 |
| 5,653,972 A | 8/1997 | Desai et al. | 424/78.04 |
| 5,719,197 A | 2/1998 | Kamios et al. | 514/772.6 |
| 5,776,445 A | 7/1998 | Cohen et al. | 424/78.04 |
| 5,811,466 A | 9/1998 | Chowhan et al. | 514/840 |
| 5,834,470 A | 11/1998 | Maurer | 514/249 |
| 6,143,799 A | 11/2000 | Chowhan et al. | 514/839 |
| 6,358,935 B1 | 3/2002 | Beck et al. | 514/58 |
| 6,365,636 B1 | 4/2002 | Chowhan et al. | 514/839 |
| 6,503,497 B2 | 1/2003 | Chowhan et al. | 424/78.04 |
| 6,562,873 B2 | 5/2003 | Olejnik et al. | 514/772.44 |
| 6,627,210 B2 | 9/2003 | Olejnik et al. | 424/427 |
| 6,641,834 B2 | 11/2003 | Olejnik et al. | 424/427 |
| 6,673,337 B2 | 1/2004 | Olejnik et al. | 424/78.04 |

FOREIGN PATENT DOCUMENTS

GB    1 463 520    2/1977

*Primary Examiner*—Zohreh Fay
(74) *Attorney, Agent, or Firm*—Patrick M. Ryan

(57) ABSTRACT

Topical solution compositions of brimonidine tartrate are disclosed. The solution compositions lack an oxidative preservative.

1 Claim, No Drawings

TOPICAL BRIMONIDINE TARTRATE FORMULATIONS THAT LACK CHLORINE DIOXIDE

This application claims priority to U.S. Provisional Application, U.S. Ser. No. 60/568,642 filed May 6, 2004.

BACKGROUND OF THE INVENTION

This invention relates to topically administrable ophthalmic formulations of brimonidine. The formulations of the present invention are solutions that contain 0.2% or less of brimonidine tartrate.

The topical use of brimonidine to lower intraocular pressure in patients with glaucoma or ocular hypertension is known. The first ophthalmic brimonidine product in the U.S. was approved by the FDA in 1996. That product, sold under the trade name Alphagan, contained brimonidine in the form of brimonidine tartrate at a concentration of 0.2%. The preservative contained in Alphagan is benzalkonium chloride, the most widely used preservative for topical ophthalmic compositions.

In 2001, a second ophthalmic brimonidine product was approved by the FDA. This product, sold under the trade name Alphagan P, contained brimonidine tartrate at a concentration of 0.15%. The preservative contained in Alphagan P is chlorine dioxide. See U.S. Pat. Nos. 5,424,078 and 6,562,873.

Chlorine dioxide is not an ideal preservative ingredient. It is an oxidative preservative. It is difficult to stabilize and is light-sensitive. Additional topical formulations of brimonidine are desired.

SUMMARY OF THE INVENTION

The compositions of the present invention are aqueous solutions of brimonidine tartrate that do not contain chlorine dioxide or any other oxidative preservative. Instead, the compositions contain a preservative ingredient consisting of a combination of polyquaternium-1 and boric acid.

DETAILED DESCRIPTION OF THE INVENTION

Unless indicated otherwise, all ingredient amounts are presented in units of % weight/volume (% w/v).

Brimonidine tartrate is a known compound that can be made by known methods and is commercially available. See, for example, German Patent No. 2,538,620. The compositions of the present invention contain 0.05-0.2% of brimonidine tartrate. Preferably, the compositions contain 0.07-0.15% of brimonidine tartrate.

In addition to brimonidine tartrate, the compositions of the present invention contain polyvinylpyrrolidone as a viscosity enhancing agent. Polyvinylpyrrolidone is commercially available from a variety of sources in different grades and in a number of molecular weights. For example, polyvinylpyrrolidone is available in at least four grades from International Specialty Products (Wayne, N.J.): Plasdone® C-15 (weight avg. MW=8K), C-30 (endotoxin-free, weight avg. MW=58,000, K-29/32 (weight avg. MW=58K) and K-90 (weight avg. MW=1300K). sodium chloride as an ionic tonicity agent. The amount of polyvinylpyrrolidone contained in the compositions of the present invention is an amount sufficient to cause the composition to have a viscosity of 2.5-3.5 cps, preferably 3.0-3.2 cps. (measured at 25° C.). In general, the compositions will contain about 1-1.5% polyvinylpyrrolidone.

The compositions of the present invention contain a combination of boric acid and sodium borate or a combination of borate and mannitol as buffering agents. The compositions contain an amount of boric acid and sodium borate sufficient to buffer the solution in a pH range of 7-7.5. In the pH range of 6.5-7, the buffering agent is preferably a combination of borate and mannitol (see, for example, U.S. Pat. No. 6,143,799, the contents of which are incorporated by reference). Preferably the compositions have a pH from 7-7.5 and contain a combination of about 0.3% boric acid and 0.02% sodium borate.

The compositions of the present invention contain polyquaternium-1 as a preservative. Polyquaternium-1 is a known compound. The amount of polyquaternium-1 contained in the compositions of the present invention will range from 0.0005-0.002%, and is preferably about 0.001%. In addition, boric acid and its ophthalmically acceptable acid addition salts, as well as borate-polyol complexes of the type described in U.S. Pat. No. 5,342,620 (Chowhan), contribute to preservative effectiveness. The water-soluble borate-polyol complexes useful in the compositions of the present invention preferably comprise borate and polyol in a molar ratio between about 1:1 and about 1:10.

The compositions of the present invention comprise a tonicity adjusting agent selected from the group consisting of metal chloride salts; mannitol; and mixtures of metal chloride salts and mannitol. Preferred metal chloride salts are those found in human tears, such sodium chloride, potassium chloride, calcium chloride and magnesium chloride. The amount of tonicity adjusting agent contained in the compositions of the present invention is an amount sufficient to cause the composition to have an osmolality of about 250-350 mOsm, preferably 270-315 mOsm. Preferably, the compositions contain 0.5-0.9% NaCl. In one embodiment, the compositions contain 0.6% NaCl, 0.13% KCl, 0.005-0.006% CaCl, 0.006-0.007% MgCl, and 0.25% mannitol.

Preferably, the concentration of potassium chloride in the compositions of the present invention does not exceed 0.15%. In a most preferred embodiment, the concentration of potassium chloride in the compositions of the present invention ranges from 0.01-0.04%.

The compositions of the present invention have a pH from 6.5-7.5, preferably from 7.0-7.4. pH can be adjusted with NaOH/HCl.

The compositions of the present invention do not contain a surfactant.

The following examples are intended to illustrate, but not limit, the present invention.

EXAMPLE 1

Topical Ophthalmic Composition

| Ingredient | % (w/v) |
| --- | --- |
| Brimonidine Tartrate | 0.15 |
| Polyquaternium-1 | 0.001 |
| Povidone K-90 | 1.2 |
| Boric Acid | 0.3 |
| Sodium Borate (decahydrate) | 0.02 |
| Calcium Chloride (dihydrate) | 0.0053 |
| Magnesium Chloride (hexahydrate) | 0.0065 |
| Potassium Chloride | 0.13 |

-continued

| Ingredient | % (w/v) |
|---|---|
| Mannitol | 0.25 |
| Sodium Chloride | 0.6 |
| NaOH/HCl | q.s. pH 6.5-7.5 |
| Purified Water | q.s. to 100 |

EXAMPLE 2

Antimicrobial Effectiveness Testing

The antimicrobial preservative effectiveness of the compositions shown in Table 2 below was determined using an organism challenge test according to the methods described in the United States Pharmacopeia 27 (USP) and European Pharmacopeia (2002 Ph. Eur., 4$^{th}$ Ed.). Samples were inoculated with known levels of gram-positive and gram-negative vegetative bacteria, yeast and mold and sampled at specified intervals to determine if the antimicrobial preservative system was capable of killing or inhibiting the propagation of organisms purposely introduced into the formulations. The rate or level of antimicrobial activity determined compliance with the USP and/or Ph. Eur. preservative efficacy standards for ophthalmic preparations. The compendial preservative standards for ophthalmic preparations are shown in Table 3 below. The results are shown in Table 4 below.

TABLE 2

| | % (w/v) | | | | |
|---|---|---|---|---|---|
| Ingredients | A | B | C | D | E |
| Brimonidine Tartrate | 0.15 | 0.15 | 0.15 | 0.15 | 0.15 |
| Polyquaternium | 0.001 + 5% xs | 0.001 + 5% xs | 0.001 + 5% xs | 0.001 + 5% xs | 0.001 + 5% xs |
| Povidone K90 | 1.2 | 1.2 | 1.2 | 1.2 | 1.2 |
| Boric Acid | 0.3 | 0.3 | 0.3 | — | — |
| Sodium Borate 10H$_2$O | 0.02 | 0.02 | 0.02 | 0.02 | 0.02 |
| Calcium Chloride 2H$_2$O | 0.0053 | 0.0053 | 0.0053 | 0.0053 | 0.0053 |
| Magnesium Chloride 6H$_2$O | 0.0065 | 0.0065 | 0.0065 | 0.0065 | 0.0065 |
| Potassium Chloride | 0.038 | 0.13 | 0.13 | 0.038 | 0.038 |
| Mannitol | — | 0.25 | 0.1 | 0.25 | 0.1 |
| Sodium Chloride | 0.65 | 0.60 | 0.60 | 0.62 | 0.66 |
| Sodium Hydroxide and/or Hydrochloric Acid | Adjust pH to 7.2 +/− 0.1 | Adjust pH to 7.2 +/− 0.1 | Adjust pH to 7.2 +/− 0.1 | Adjust pH to 7.2 +/− 0.1 | Adjust pH to 7.2 +/− 0.1 |
| Purified Water | QS to 100 | QS to 100 | QS to 100 | QS to 100 | QS to 100 |

TABLE 3

| | Log Reduction of Organism Population | | |
|---|---|---|---|
| Time Pull | USP | Ph. Eur. A (Target) | Ph. Eur. B (Min) |
| For Bacteria: | | | |
| 6 hours | — | 2 | — |
| 24 hours | — | 3 | 1 |
| 7 days | 1 | — | 3 |
| 14 days | 3 | — | — |
| 28 days | NI | NR | NI |
| For Fungi: | | | |
| 7 days | — | 2 | — |
| 14 days | NI | — | 1 |
| 28 days | NI | NI | NI |

NR = No organisms recovered
NI = No increase at this or any following time pulls
— = No requirement at this time pull

TABLE 4

| Formulation | 0.25 day | 1 day | 7 days | 14 days | 21 days | 28 days |
|---|---|---|---|---|---|---|
| | S. aureus | | | | | |
| A | 3.3 | 4.6 | 5.1 | 5.1 | 5.1 | 5.1 |
| B | 3.04 | 3.60 | 4.98 | 4.98 | 4.98 | 4.98 |
| C | 3.3 | 4.2 | 5.1 | 5.1 | 5.1 | 5.1 |
| D | 3.5 | 4.5 | 5.1 | 5.1 | 5.1 | 5.1 |
| E | 3.5 | 4.3 | 5.1 | 5.1 | 5.1 | 5.1 |
| | P. aeruginosa | | | | | |
| A | 2.2 | 4.5 | 5.0 | 5.0 | 5.0 | 5.0 |
| B | 2.54 | 4.16 | 5.06 | 5.06 | 5.06 | 5.06 |
| C | 2.2 | 3.8 | 4.8 | 4.8 | 4.8 | 4.8 |
| D | 2.9 | 4.8 | 4.8 | 4.8 | 4.8 | 4.8 |
| E | 2.7 | 4.8 | 4.8 | 4.8 | 4.8 | 4.8 |
| | E. coli | | | | | |
| A | 3.5 | 5.1 | 5.1 | 5.1 | 5.1 | 5.1 |
| B | 3.98 | 4.98 | 5.14 | 5.14 | 5.14 | 5.14 |
| C | 4.1 | 5.2 | 5.2 | 5.2 | 5.2 | 5.2 |
| D | 5.2 | 5.2 | 5.2 | 5.2 | 5.2 | 5.2 |
| E | 4.7 | 5.2 | 5.2 | 5.2 | 5.2 | 5.2 |
| | C. albicans | | | | | |
| A | X | X | 1.5 | 1.8 | 2.4 | 3.4 |
| B | X | X | 0.46 | 0.78 | 1.20 | 1.70 |
| C | X | X | 0.8 | 1.1 | 1.7 | 2.8 |
| D | X | X | 0.9 | 1.1 | 1.8 | 2.8 |
| E | X | X | 0.8 | 1.0 | 1.8 | 2.7 |

TABLE 4-continued

| Formulation | 0.25 day | 1 day | 7 days | 14 days | 21 days | 28 days |
|---|---|---|---|---|---|---|
| | | | *A. niger* | | | |
| A | X | X | 1.1 | 1.2 | 1.0 | 1.0 |
| B | X | X | 1.52 | 1.46 | 1.58 | 1.56 |
| C | X | X | 1.2 | 1.7 | 1.8 | 1.8 |
| D | X | X | 1.6 | 1.6 | 1.9 | 1.8 |
| E | X | X | 1.7 | 1.6 | 1.8 | 1.7 |

X = not tested

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topically administrable ophthalmic solution consisting essentially of
   a) 0.07-0.15% (w/v) brimonidine tartrate;
   b) 0.001% (w/v) polyquatermium-1;
   c) 0.3% (w/v) boric acid;
   d) 0.02% (w/v) sodium borate;
   e) 1.0-1.5% (w/v) polyvinylpyrrolidone;
   f) sodium chloride;
   g) potassium chloride;
   h) calcium chloride;
   i) magnesium chloride;
   j) mannitol; and
   k) water,
   wherein the composition has an osmolality of 270-315 mOsm and a pH from 7.0-7.5.

* * * * *